United States Patent [19]

Lillig et al.

[11] Patent Number: 5,210,256
[45] Date of Patent: May 11, 1993

[54] 2-METHYL-3-CHLOROPROPYL-CYCLOHEXYLDICHLOROSILANE

[75] Inventors: Bernhard Lillig; Claus-Dietrich Seiler, both of Rheinfelden, Fed. Rep. of Germany

[73] Assignee: Huels Aktiengesellschaft, Marl, Fed. Rep. of Germany

[21] Appl. No.: 954,164

[22] Filed: Sep. 29, 1992

[30] Foreign Application Priority Data

Oct. 23, 1991 [DE] Fed. Rep. of Germany ....... 4134977

[51] Int. Cl.$^5$ .............................. C07F 7/08; C07F 7/18
[52] U.S. Cl. ..................................................... 556/488
[58] Field of Search .......................................... 556/488

[56] References Cited

U.S. PATENT DOCUMENTS 4,053,496 10/1977 Föry et al. ..................... 556/488 X
4,053,497 10/1977 Föry et al. ..................... 556/488 X
4,659,852 4/1987 Shinohara et al. ............. 556/488 X

*Primary Examiner*—Paul F. Shaver
*Attorney, Agent, or Firm*—Felfe & Lynch

[57] ABSTRACT

The novel compound 2-methyl-3-chloropropyl-cyclohexyldichlorosilane is prepared by reacting cyclohexyldichlorosilane with 2-methyl-3-chloropropene or by reacting 2-methyl-3-chloropropyldichlorosilane with cyclohexene, each in the presence of platinum or a platinum compound.

5 Claims, No Drawings

2-METHYL-3-CHLOROPROPYL-CYCLOHEXYL-DICHLOROSILANE

FIELD OF THE INVENTION

This invention relates to the novel compound 2-methyl-3-chloropropyl-cyclohexyldichlorosilane, as well as to a process for the preparation of this compound.

BACKGROUND OF THE INVENTION

It is known to employ bi-functional diorganosilane compounds for the modification of silicones. For this purpose, those compounds have recently acquired particular interest which contain in the molecule as organo component, in addition to a non-reactive radical such as alkyl cycloalkyl, a radical which comprises a key atom, preferably a chlorine atom, for the introduction of functional groups. The introduction of the desired functional groups may be effected after incorporation of the molecule into siloxane chains or also after esterification of the silicon-functional radical of the starting compound.

OBJECT OF THE INVENTION

It is an object of the present invention to provide a novel bi-functional diorganosilane compound which can be used for the modification of silicones.

Other objects and advantages of the present invention will become apparent as the description thereof proceeds.

DESCRIPTION OF THE INVENTION

The above object is achieved in accordance with the present invention by providing the novel compound 2-methyl-3-chloropropyl-cyclohexyldichlorosilane and a process for the preparation of this compound.

2-methyl-3-chloropropyl-cyclohexyldichlorosilane is prepared in accordance with the present invention by reacting cyclohexyldichlorosilane with 2-methyl-3-chloropropene, or by reacting 2-methyl-3-chloropropyl-dichlorosilane with cyclohexene each in the presence of platinum or a platinum compound.

In the preparation of 2-methyl-3-chloropropyl-cyclohexyldichlorosilane, the quantitative ratio of the two reaction partners is preferably chosen so that a molar excess of unsaturated compound per gram atom of the reacting hydrogen of the hydrogensilane is provided. Accordingly, about 1.2 to 1.4 mols of the olefinic compound per mol of hydrogen silane are used.

The reaction of the reactants takes place in the presence of platinum or a platinum compound as catalysts. Metallic platinum is used in the form of platinum sponge, preferably deposited on activated charcoal. Examples of suitable platinum compounds are the simple platinum compound of the formula $$H_2PtCl_6 \cdot 6\ H_2O$$

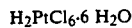

or the complex platinum compound mesityl-platinumdichloride.

When 2-methyl-3-chloropropene is used as the olefinic reaction component, the reaction forms not only 2-methyl-3-chloropropyl-cyclohexyldichlorosilane but also cyclohexyltrichlorosilane which results from the β-decomposition of 1,1-dimethyl-2-chloroethyl-cyclohexyldichlorosilane which is formed to a limited extent during the reaction. The reaction products differ in their boiling points, so that a separation by distillation in accordance with conventional methods is possible.

When cyclohexene is used as the olefinic reaction component, a side reaction of this type does not occur.

The reaction of the hydrogensilane with the particular olefin proceeds exothermically and may be performed within wide temperature ranges. The reaction temperature should, if possible, not be less than 80° C. and no higher than 180° C.

Depending upon the particular method of synthesis which is chosen, the reaction of the reactants is performed at normal or elevated pressure. Thus, in order to avoid long reaction periods in the preparation of 2-methyl-3-chloropropyl-cyclohexyldichlorosilane, it is recommended to perform the reaction at elevated pressure if the olefinic component is provided and the silane component is metered into it at a rate commensurate with the progress of the reaction. On the other hand, if the reaction is performed by providing the silane component and metering the olefin into it, the reaction can be performed at normal pressure and at temperatures below the boiling point of the hydrogensilane.

The following examples illustrate the present invention and will enable others skilled in the art to understand it more completely. It should be understood, however, that the invention is not limited solely to the particular examples given below.

EXAMPLE 1

The following apparatus was constructed of steel:

A round bottom steel flask with a capacity of about 12 liters and heatable with steam by way of an emersion heater was connected by means of a steel line with the lower portion of a condenser having a cooling surface of about 0.5 m² mounted above the round bottom flask. The lower portion of the condenser was connected with the lower portion of the round bottom flask through a steel line, about 2 meters long, extending downwardly by way of a bent tube. The round bottom flask itself was equipped with a pressure gauge and a temperature gauge. The condenser was operated with water as the cooling agent and was turned off at the beginning of the run.

1950 g (21.5 mols) of 2-methyl-3-chloropropene and 22 ml of a catalyst solution, consisting of 1 g of $H_2PtCl_6 \cdot 6\ H_2O$ dissolved in 23 ml of acetone, were introduced into the evacuated round bottom flask. By introducing steam into the emersion heater, the system was heated to a temperature of about 110° C., whereby an internal apparatus pressure of 0.25 MPa developed. Water was then supplied to the condenser above the flask to cause condensation of the 2-methyl-3-chloropropene vapors. Over a period of 2 hours 4600 g (25.1 mols) of cyclohexyldichlorosilane were introduced into the system. The initiation of the reaction was signaled by an increase of the internal flask temperature. Three hours after completion of the cyclohexyldichlorosilane introduction, an additional amount of 1300 g (14.4 mols) of 2-methyl-3-chloropropene together with 15 ml of the catalyst solution were introduced over a period of 45 minutes into the reaction mixture in the flask. After a total reaction time of 13 hours, the reaction was discontinued, and the reaction mixture was drained off and worked up by distillation.

5228 g (19.1 mols) of 2-methyl-3-chloropropyl-cyclohexyldichlorosilane were obtained, which corresponds to a yield of 76%, based on the amount of cyclohexyldichlorosilane reactant.

The structure of the novel compound was identified by means of elemental and GC/MS-analysis as well as by NMR-spectra.

| Molecular weight: | theoretical | 273.71 g/mol |
| --- | --- | --- |
|  | found | 277.3 g/mol |
| Density ($d_4^{20}$) |  | 1.154 g/cm$^3$ |
| Dynamic viscosity: |  | 12.5 mPa·s |
| Boiling point (0.1 hPa): |  | 121° C. |
| Elemental analysis: | theory | found |
| C | 43.9% | 43.7% |
| H | 6.9% | 7.0% |
| Si | 10.2% | 10.1% |
| Cl | 39.0% | 39.2% |

Accordingly, the reaction product thus obtained has the structural formula

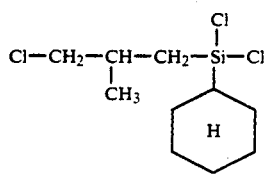

EXAMPLE 2

3831 g (20 mols) of 2-methyl-3-chloropropyldichlorosilane together with 12 ml of the catalyst solution described in Example 1 were introduced into a four-neck round bottom flask equipped with a dropping funnel, reflux cooler, stirrer and temperature regulator. While stirring, the contents of the flask were heated to about 110° C., and this temperature was maintained until completion of the subsequent reaction. Over a period of 6 hours 1807 g (22 mols) of cyclohexene were added to the flask contents by way of the dropping funnel. After passage of 3 hours, an additional 12 ml of the catalyst solution were added. The total reaction period was 19 hours. Thereafter, the reaction mixture was worked up by distillation.

5200 g (19 mols) of 2-methyl-3-chloropropyl-cyclohexyldichlorosilane were obtained, which corresponds to a yield of 95%, based on the amount of 2-methyl-3-chloropropyldichlorosilane reactant.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. 2-methyl-3-chloropropyl-cyclohexyldichlorosilane.

2. The method of preparing 2-methyl-3-chloropropylcyclohexyldichlorosilane which comprises reacting cyclohexyldichlorosilane with 2-methyl-3-chloropropene in the presence of platinum or a platinum compound.

3. The method of preparing 2-methyl-3-chloropropylcyclohexyldichlorosilane, which comprises reacting 2-methyl-3-chloropropyldichlorosilane with cyclohexene in the presence of platinum or a platinum compound.

4. The method of claim 2, wherein the reaction is performed at a temperature of 80° to 180° C.

5. The method of claim 3, wherein the reaction is performed at a temperature of 80° to 180° C.

* * * * *